(12) United States Patent
Kilcher et al.

(10) Patent No.: US 6,905,244 B2
(45) Date of Patent: Jun. 14, 2005

(54) HOLDER FOR DIGITAL SENSORS FOR DENTISTRY

(75) Inventors: Beat Kilcher, Luganese (CH); Marco Da Rold, Vaglio (CH)

(73) Assignee: Kerrhawe SA, Bioggio (CH)

( * ) Notice: Subject to any disclaimer, the term of this patent is extended or adjusted under 35 U.S.C. 154(b) by 0 days.

(21) Appl. No.: 10/672,378

(22) Filed: Sep. 26, 2003

(65) Prior Publication Data

US 2004/0096040 A1 May 20, 2004

(30) Foreign Application Priority Data

Sep. 30, 2002 (CH) ........................................ 20021632/02

(51) Int. Cl.⁷ ................................................ A61B 6/14
(52) U.S. Cl. .......................... 378/170; 378/168; 378/191
(58) Field of Search ................................ 378/168–170, 378/181, 191

(56) References Cited

U.S. PATENT DOCUMENTS

| | | | |
|---|---|---|---|
| 1,576,477 A | 3/1926 | Weins ........................ 378/168 |
| 2,688,096 A | 8/1954 | Galliano et al. ............... 250/70 |
| 3,771,781 A | * 11/1973 | Lackey et al. ............... 269/218 |
| 4,057,732 A | 11/1977 | Klauser ....................... 250/479 |
| 5,317,619 A | * 5/1994 | Hellmick et al. ........... 378/173 |
| 5,799,058 A | 8/1998 | Willis et al. ................. 378/168 |
| 6,203,195 B1 | * 3/2001 | Willis ......................... 378/168 |
| 6,276,827 B1 | * 8/2001 | Nakamura et al. .......... 378/167 |
| 6,343,875 B1 | 2/2002 | Eppinger et al. ........... 378/170 |

FOREIGN PATENT DOCUMENTS

| | | |
|---|---|---|
| CA | 2 324 871 | 4/2002 |
| FR | 1088070 | 3/1995 |

* cited by examiner

*Primary Examiner*—Craig E. Church
*Assistant Examiner*—Jurie Yun
(74) *Attorney, Agent, or Firm*—Wood, Herron & Evans

(57) ABSTRACT

In the holder set for digital sensors for dentistry, the holders for each kind of radiograph such as periapical radiographs of front teeth (anterior teeth) and lateral teeth (posterior teeth), on one hand, and bitewing radiographs, on the other hand, can be used for all sensor formats, the sensors being seized in the respective holders in a self-centered manner by two arms independently of their format.

9 Claims, 3 Drawing Sheets

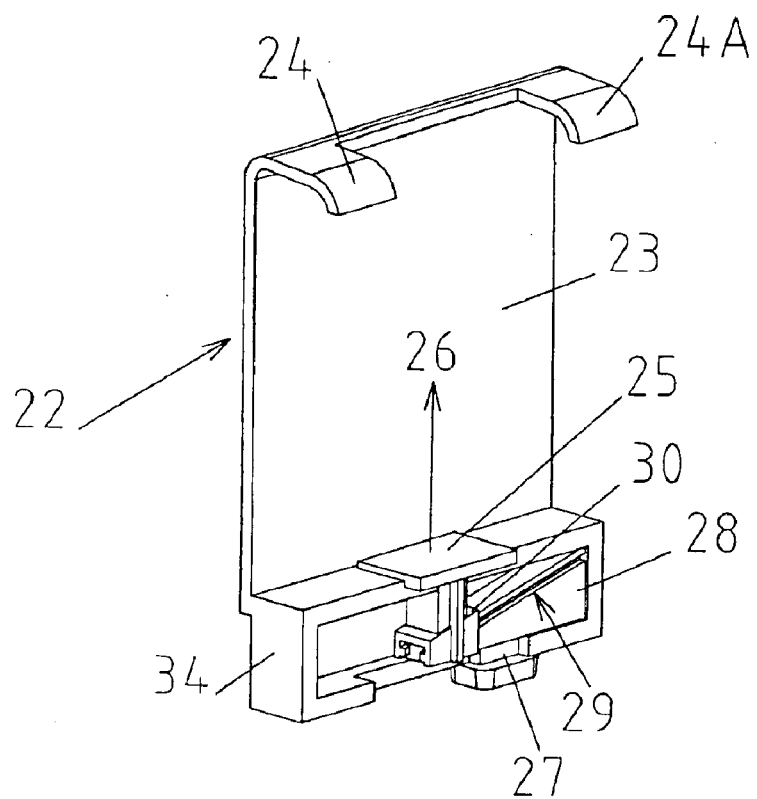
Fig. 6
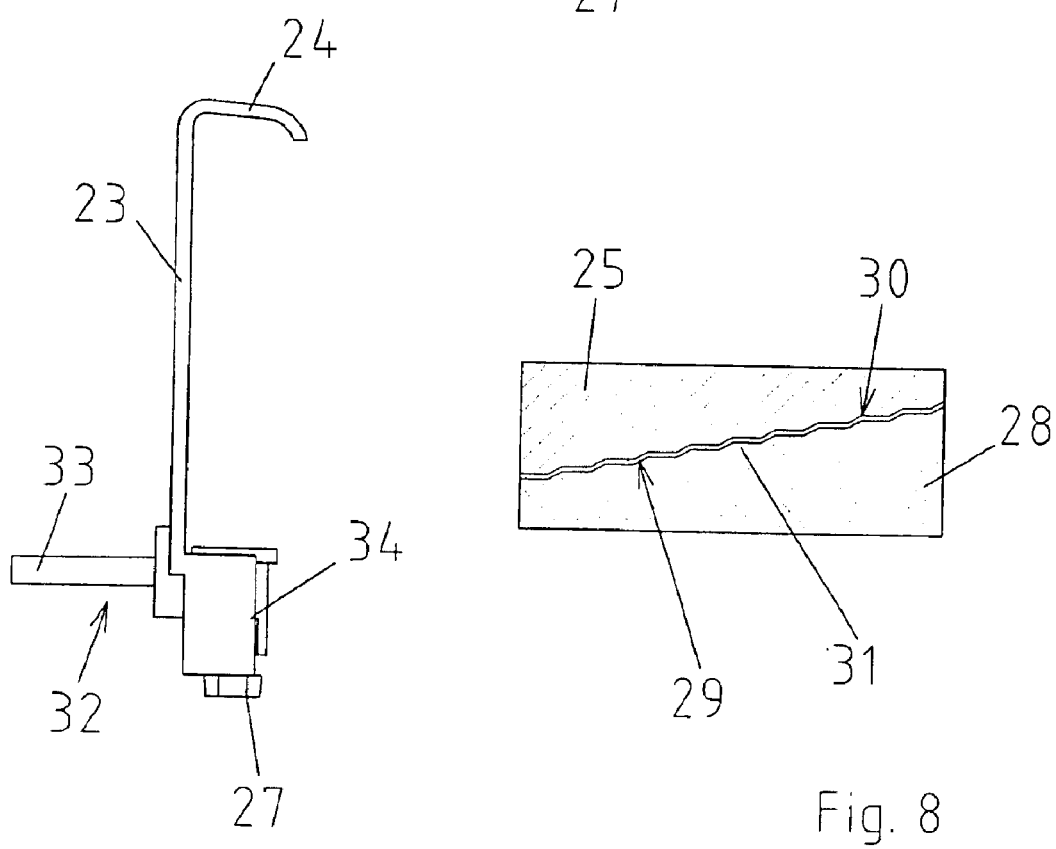
Fig. 7
Fig. 8

HOLDER FOR DIGITAL SENSORS FOR DENTISTRY

FIELD OF THE INVENTION

The present invention refers to a holder set for digital sensors for dentistry, each holder of the set comprising at least one displaceable arm.

BACKGROUND OF THE INVENTION

Until lately, radiographs have been recorded on X-ray films that have been exposed and subsequently developed. Since X-ray films of this kind have determined standard formats, the sizes of the holders resp. of the clamping portions intended for receiving the X-ray films are standardized too. Up to now, the main problem with regard to such X-ray film holders has been to enable radiographs of the bitewing and of other areas of the teeth with a minimum number of different holders, while the film formats are mostly clamped either transversely or longitudinally.

Recently, a new imaging technique has been developed where digital image sensors are directly connected to a computer by a cable in order to directly display or store the radiographs on the latter.

In contrast to X-ray films, the different digital sensor products have different dimensions with regard to length and width and to thickness. Moreover, sensors of this kind comprise a cable, thereby making the correct positioning of such sensors problematic.

PRIOR ART

A number of sensor holders are already known, e.g. according to U.S. Pat. No. 6,203,195, disclosing a sensor holder whose holder arm is extensible to enable the retention of different formats. Although it is already suggested here to use different formats, the universal application of this holder is limited by its construction.

WO/49 945 discloses another sensor holder where a holder arm is extensible for attaching sensors of different dimensions. Here also, the construction does not allow the universal application of the most diverse sensors.

SUMMARY OF THE INVENTION

On the background of this prior art, it is the object of the present invention to provide a set of sensor holders that allows radiographs with all of the available digital sensors in the area of the anterior teeth and in the lateral area, i.e. in the periapical tissue, as well as horizontal and vertical bitewing images, while providing a good positioning, on one hand, and maximum comfort for the patient, on the other hand. This object is attained by a holder set wherein for each kind of radiograph such as periapical radiographs and radiographs of lateral and anterior teeth, on one hand, and bitewing radiographs, on the other hand, a respective holder is used for all sensor formats, the sensors being seized in the respective holders in a self-centered manner by two arms independently of their format, and by a holder set wherein for each kind of radiograph such as periapical radiographs and radiographs of lateral and of anterior teeth, a respective holder is used for all sensor formats, the sensor clamp comprising a clamping jaw for pressing the sensor against grippers independently of its format. The further claims indicate respective preferred embodiments.

BRIEF DESCRIPTION OF THE DRAWINGS

The invention will be explained in more detail hereinafter with reference to drawings of exemplifying embodiments.

FIG. 6 shows a partly sectioned view of another exemplifying embodiment of a clamping portion for a holder intended for periapical images;

FIG. 7 shows the clamping portion of FIG. 6 in a side view; and

FIG. 8 shows a detail of FIG. 6.

DESCRIPTION OF PREFERRED EMBODIMENTS

Figure 1:
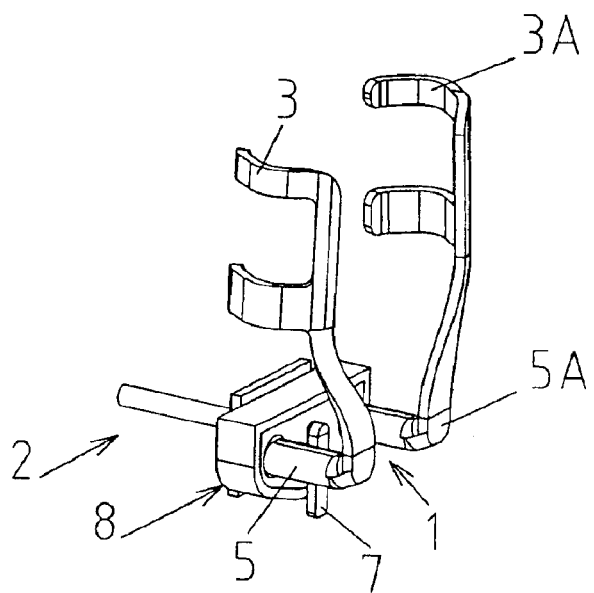
FIG. 1 shows a first exemplifying embodiment of the clamping portion of a holder intended for periapical radiographs.
Figure 2:
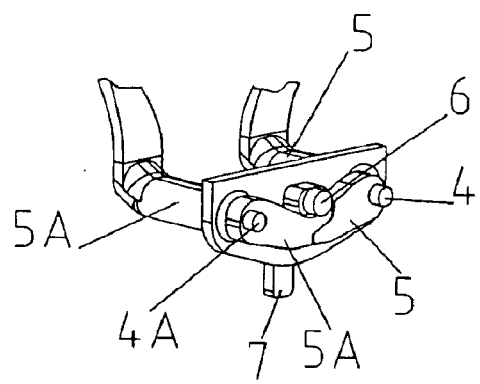
FIG. 2 shows a detail of the clamping portion of FIG. 1.
Figure 3:
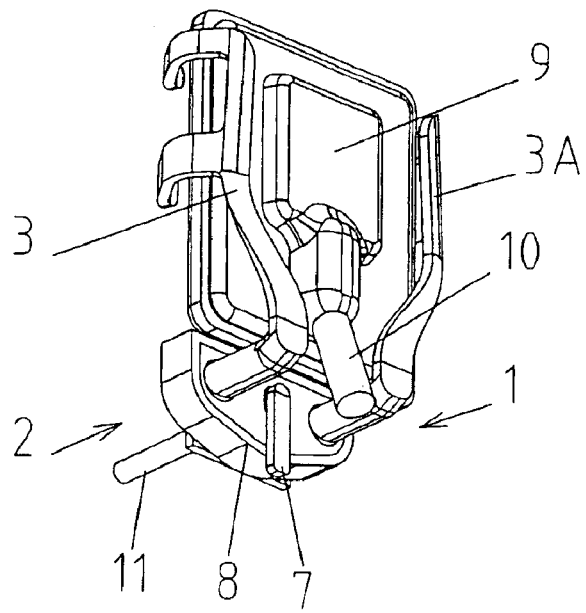
FIG. 3 shows the clamping portion of FIG. 1 with a vertically disposed sensor.

FIGS. 1 to 3 show a first exemplifying embodiment of a sensor clamp of a holder where the two arms with the retaining strip are moved in a self-centering manner. Sensor clamp 1 of holder 2 comprises two arms 3 and 3A that are hinged on respective axles 4 and 4A and comprise respective angled levers 5, 5A actuated by a camshaft 6 in such a manner that the levers are pivoted down in FIG. 2 and the arms are thus swung inwards. The camshaft is under the action of a locking lever 7 for unlocking the arms, whereby they are swung to the open position. The camshaft and the levers are arranged in an enclosure 8.

This holder is particularly suitable for periapical radiographs of the anterior teeth, and it appears in FIG. 3 that the digital sensor 9 with cable 10 is laterally clamped and the arms are designed such that little space is required laterally. Furthermore, it appears in FIG. 3 that the sensor clamp does not project beyond sensor 9.

FIG. 1 or 3 show a portion 11 of holder 2 whose constructive principle is similar to that of the holder according to EP-B-397 599. Thus, both the bite piece and the cranked indicator rod are the same or similar as in the cited European Patent while the spring-actuated X-ray film clamp has been replaced by the clamping portion 1 of FIG. 1.

Figure 4:
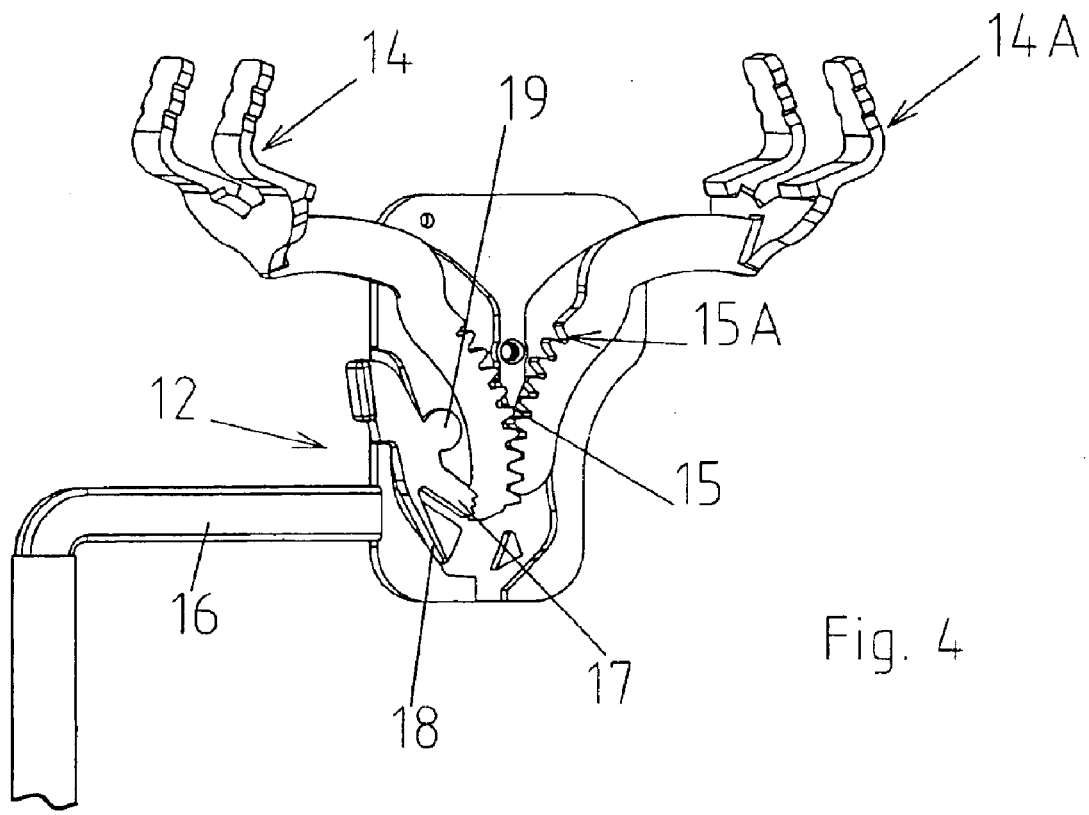
FIG. 4 shows a second exemplifying embodiment of a clamping portion for a holder intended for bitewing images without the cover.
Figure 5:
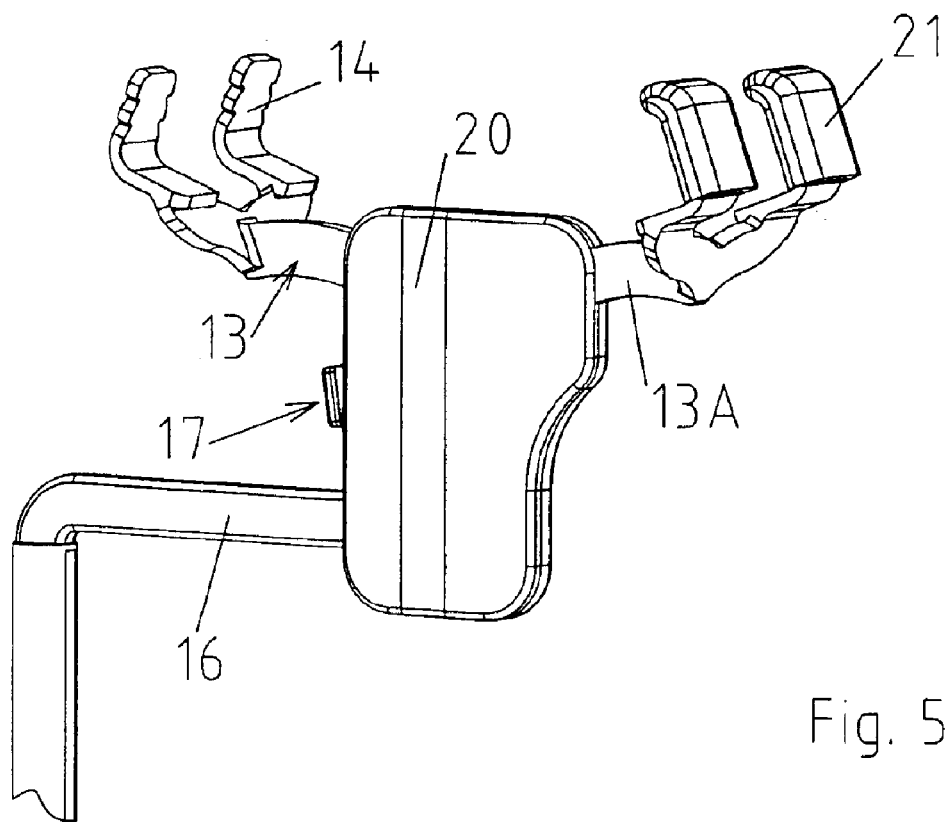
FIG. 5 shows the clamping portion of FIG. 4 viewed from the opposite side.

FIGS. 4 and 5 illustrate a holder for bitewing radiographs including a sensor clamp instead of the x-ray clamp. X-ray film holders for bitewing radiographs are known in the art and have been marketed for a long time by the applicant of the present invention, amongst others. Therefore, the parts that are not or not completely illustrated in FIGS. 4 and 5, such as the cranked indicator rod, are not described in more detail. In analogy to the sensor clamp according to FIGS. 1 to 3, the arms also move symmetrically, so that the sensor is always aligned to the indicator rod resp. to the X-ray tube in the same way independently of the dimensions of the sensor.

In FIG. 4, sensor clamp 12 is illustrated without its cover and schematically, and the two arms 13 and 13A with grippers 14 and 14A are visible. The arms are followed by curved portions provided with toothed racks 15 and 15A, the two toothed racks meshing with each other. Furthermore, in FIG. 4, a part of indicator rod 16 is visible. The movement of the toothed racks is influenced by a catch 17, the catch being self-locking so that the arms remain in any position they have attained. Moreover, the catch comprises a restoring spring 18, whereby one end of the catch is constantly acting upon one of the curved toothed racks, thus providing the self-locking action. The catch turns on pivot 19.

The solution using curved toothed racks allows a very slim design of the entire spreading and locking mechanism, thereby allowing a very slim design of bite piece 20, which is formed by the enclosure of the mechanism, see FIG. 5, so that the entire holder is more comfortable for the patient than anterior holders. The arms, resp. the clamping jaws with the grippers are so designed that they may accommodate any sensor geometry, i.e. they have a prismatic shape, as appears clearly in FIG. 5.

In a variant of the embodiment, rubber pads 21 are plugged onto grippers 13, 13A. For this purpose, it is useful if the grippers have a structure whereby such rubber pads are retained.

In FIGS. 6 to 8, a second embodiment of a periapical sensor holder for posterior teeth (lateral teeth) is illustrated where the sensor is clamped from the bottom up instead of being seized laterally as in the preceding exemplifying embodiments.

Sensor clamp 22 may be mounted on the same holder as in the preceding examples, i.e. the plate is mounted directly adjacent the bite piece. The sensor clamp comprises a wall 23 provided with two integrally formed grippers 24, 24A intended for the retention of the sensor. In the lower portion of the clamp, a clamping jaw 25 is arranged which is upwardly displaceable according to arrow 26 in order to clamp the sensor. A locking knob 27 is provided on locking portion 28, the latter comprising an inclined plane 29 that actuates another inclined plane 30 of clamping jaw 25.

As locking portion 28 is moved from the right to the left in the drawing, the clamping jaw is pushed upwards. As shown in FIG. 8, both inclined planes 29 and 30 are provided with small teeth 31 inhibiting any movement of the two inclined planes on each other such that the clamping jaw always remains in the adjusted position. The self-locking mechanism is released by an opening motion in which the adhesion is overcome. This clamping mechanism is space-saving, so that the holder is slim and does not disturb.

FIG. 7 further shows that this sensor clamp may be arranged on a holder of the prior art instead of the usual film clamp. A part of indicator rod 33 appears in the illustration of holder 32. The clamping mechanism is accommodated in an enclosure 34.

All sensor clamps of the invention have in common that they allow a problem-free and precise retention of the digital sensors with hygienic pouches or other protective envelopes and that no other plastic materials are present between the sensor and the X-ray tube. Also, as clearly follows from the description, they allow the retention of sensors of all dimensions. It further follows from the description that the sensors are always seized rather than being pushed into the clamp as the arms can always be opened to receive the sensor and subsequently retain it.

What is claimed is:

1. A holder for digital dental sensors, comprising:
 a holder housing; and
 first and second arms rotatably coupled to said housing for movement between a first position wherein the sensor is removable from the holder, and a second position wherein the sensor is grasped between said arms;
 said housing and said arms sized to fit within the mouth of a patient.

2. The holder of claim 1, further comprising:
 first and second levers associated with said first and second arms, respectively, and operable to move said first and second arms to and between said first and second positions; and
 a cam engagable with said first and second levers to move said first and second arms to and between said first and second positions.

3. The holder of claim 2, wherein said first and second arms are pivotally coupled to said housing.

4. The holder of claim 1, further comprising:
 a plurality of gear teeth formed on each of said first and second arms, said gear teeth intermeshing to move said first and second arms between said first and second positions.

5. The holder of claim 4, wherein said first and second arms have arcuate shapes, at least proximate said gear teeth.

6. The holder of claim 4, further comprising:
 a catch engagable with at least one of said first and second arms to maintain said first and second arms in said first position, said second position, or any position therebetween.

7. The holder of claim 6, further comprising:
 a biasing member associated with said catch and cooperating with said catch to maintain said first and second arms in said first position, said second position, or any position therebetween.

8. A holder for digital dental sensors, comprising:
 a holder housing;
 first and second opposed clamping members supported by said holder housing and sized to fit within the mouth of a patient, said first clamping member movable in directions toward and away from said second clamping member to respectively grip and release the digital sensor therebetween;
 a first inclined plane associated with said first clamping member; and
 a second inclined plane abutting said first inclined plane and movable relative to said first inclined plane to move said first clamping member toward and away from said second clamping member.

9. The holder of claim 8 further comprising teeth formed in said first and second inclined planes, said teeth cooperating to inhibit relative movement of said first and second inclined planes to thereby maintain a position of said first clamping member relative to said second clamping member.

* * * * *